United States Patent
Brunelle et al.

(10) Patent No.: US 10,222,053 B2
(45) Date of Patent: Mar. 5, 2019

(54) BATHTUB HAVING AT LEAST ONE WINDOW AND METHOD OF MAKING A WINDOW IN A BATHTUB

(71) Applicant: GESTION ULTRA INTERNATIONALE INC., St-Nicolas (CA)

(72) Inventors: Henry Brunelle, Quebec (CA); Louis Gendreau, Sainte-Marie (CA); Danny Grenier, Quebec (CA); Guy Baillargeon, Lévis (CA); Guillaume Savard, Quebec (CA); Marie-Hélène Poirier, Lévis (CA)

(73) Assignee: GESTION ULTRA INTERNATIONALE INC., St-Nicolas (CA)

(*) Notice: Subject to any disclaimer, the term of this patent is extended or adjusted under 35 U.S.C. 154(b) by 0 days.

(21) Appl. No.: 16/004,950

(22) Filed: Jun. 11, 2018

(65) Prior Publication Data
US 2018/0356087 A1    Dec. 13, 2018

Related U.S. Application Data

(60) Provisional application No. 62/518,265, filed on Jun. 12, 2017.

(51) Int. Cl.
*F21V 33/00* (2006.01)
*A47K 3/00* (2006.01)
(Continued)

(52) U.S. Cl.
CPC ............ *F21V 33/004* (2013.01); *A47K 3/001* (2013.01); *F21V 31/005* (2013.01); *F21Y 2115/10* (2016.08)

(58) Field of Classification Search
CPC ...... F21V 33/004; F21V 31/005; A47K 3/001
See application file for complete search history.

(56) References Cited

U.S. PATENT DOCUMENTS

| 4,535,489 A | 8/1985 | Elkins |
| 5,217,292 A | 6/1993 | Chalberg |
| (Continued) | | |

FOREIGN PATENT DOCUMENTS

| CN | 202112975 U | 1/2012 |
| CN | 205697464 U | 11/2016 |
| EP | 1038484 A2 | 9/2000 |

OTHER PUBLICATIONS

Amazon, Jetted Whirlpool Hydrotherapy Bathub Tub w/ Heat Radio Chromatherapy 002A, retrieved from Internet Feb. 27, 2017.
(Continued)

*Primary Examiner* — Thomas M Sember
(74) *Attorney, Agent, or Firm* — Norton Rose Fulbright Canada LLP; Alexandre Daoust

(57) ABSTRACT

The bathtub generally has a wall having a translucent inner layer defining a cavity for receiving water. The bathtub has at least one translucent outer reinforcement member which is secured to a portion of the translucent inner layer, thus forming at least one window with the corresponding portion of the translucent inner layer. The bathtub has a corresponding light source which faces the translucent outer reinforcement member for lighting through the window, into the cavity. The wall further has an outer reinforcement layer covering the translucent inner layer around the at least one window.

18 Claims, 9 Drawing Sheets

(51) Int. Cl.
*F21V 31/00* (2006.01)
*F21Y 115/10* (2016.01)

(56) References Cited

U.S. PATENT DOCUMENTS

| | | | |
|---|---|---|---|
| 6,021,960 | A | 2/2000 | Kehat |
| 6,467,103 | B1 | 10/2002 | Gardenier et al. |
| 6,539,561 | B2 | 4/2003 | Shimizu |
| 6,601,247 | B2 | 8/2003 | Shimizu |
| 6,702,451 | B1 | 3/2004 | Daane |
| 6,752,517 | B2 | 6/2004 | Hildebrand et al. |
| 6,886,958 | B1 * | 5/2005 | Grant ................. E03C 1/18 362/101 |
| 6,942,354 | B2 * | 9/2005 | Metayer ............... F21V 15/01 362/101 |
| 7,490,369 | B2 | 2/2009 | Cunningham |
| 8,042,962 | B2 * | 10/2011 | Fuentes ............... F21V 33/004 362/234 |
| 9,114,060 | B2 | 8/2015 | Ciechanowski et al. |
| 2014/0324136 | A1 | 10/2014 | Hatley |

OTHER PUBLICATIONS

Hydro Massage Products, Cromatherapy Lighting System, Led Chromatherapy Light Kit, retrieved from Internet Feb. 27, 2017.
Kholer, Chromatherapy, retrieved from Internet Feb. 27, 2017.
LightingETC., Steam Spa G-CLIGHT SteamSpa Chrometherapy Lighting System SteamSpa, retrieved from Internet Feb. 27, 2017.

* cited by examiner

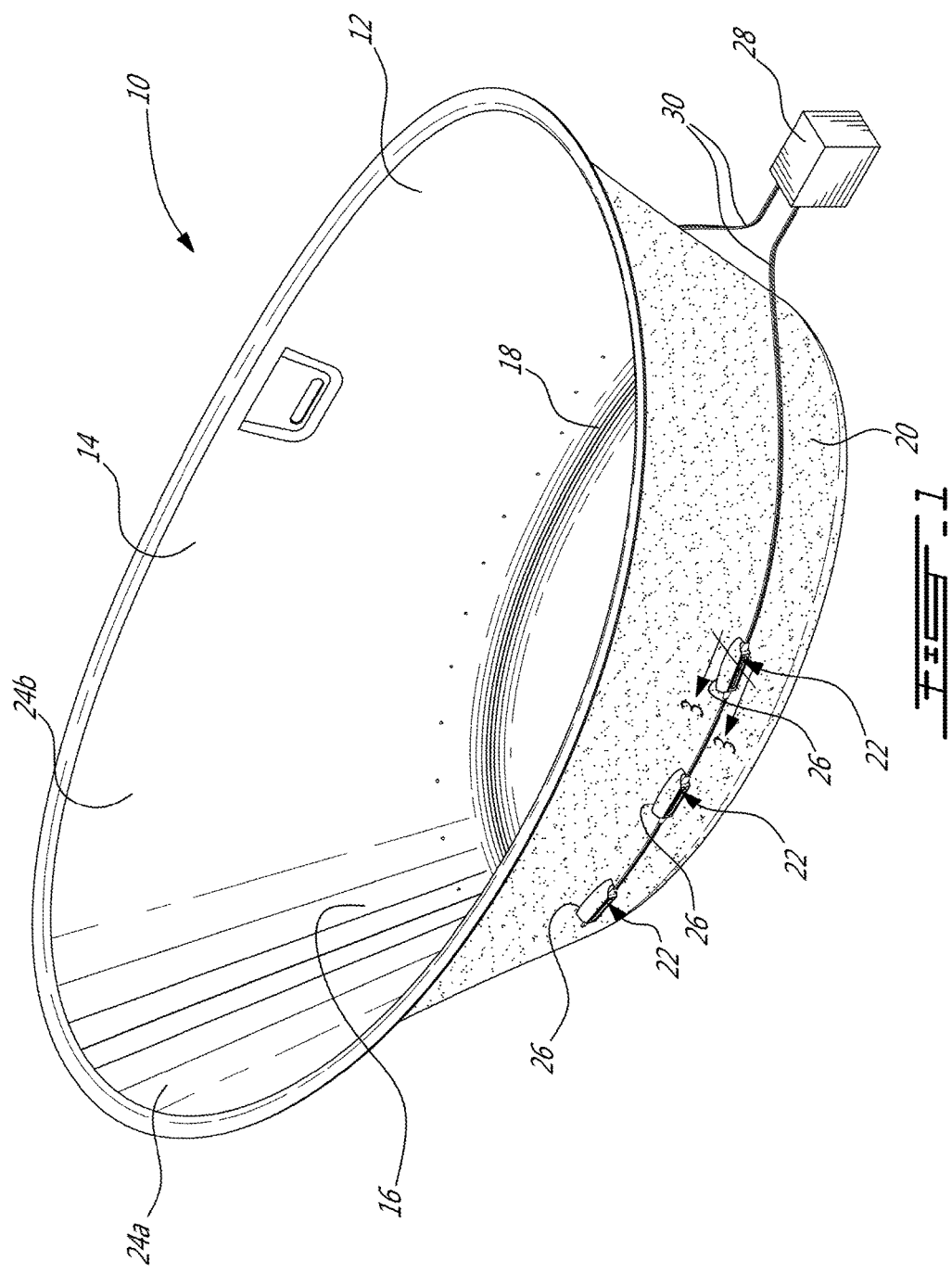

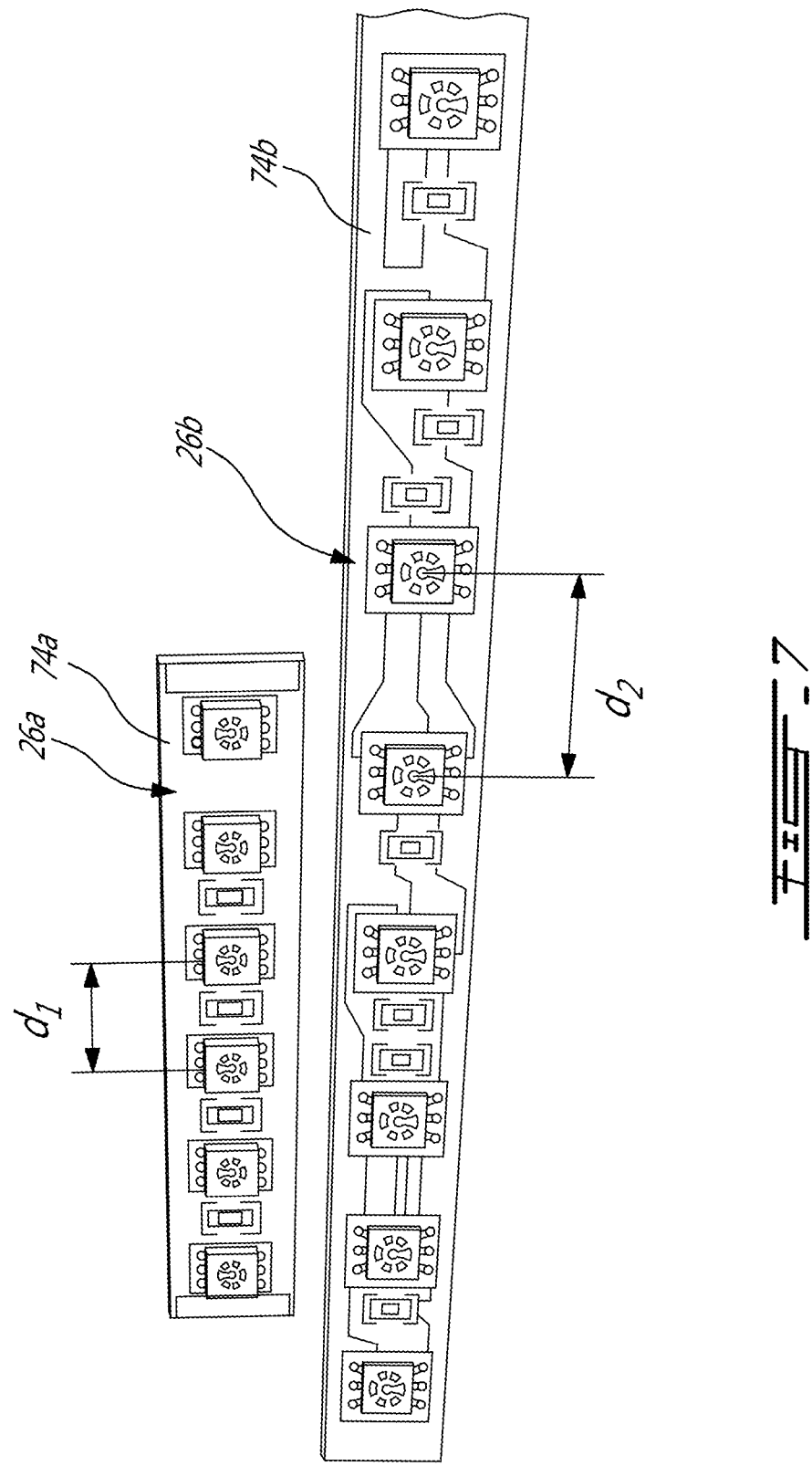

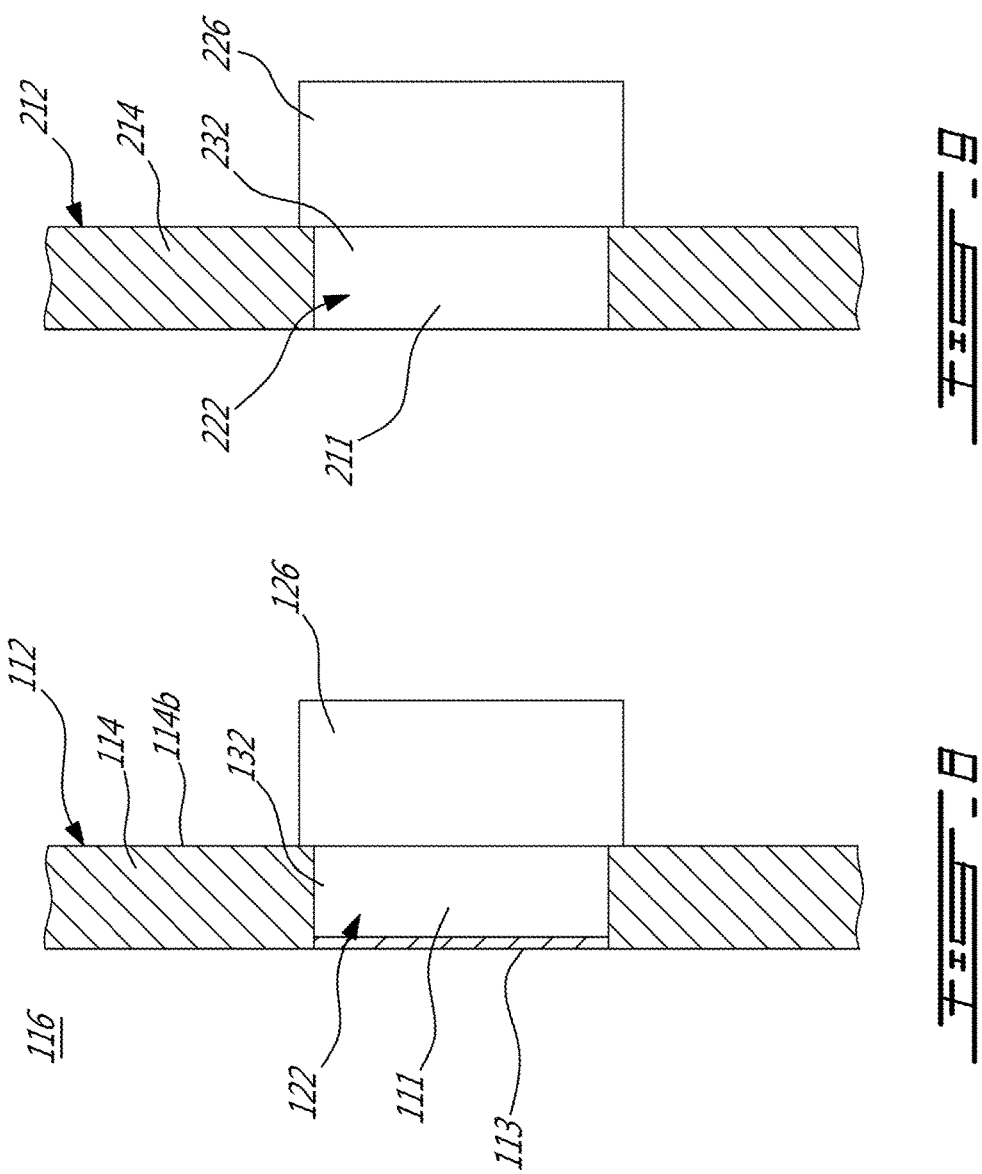

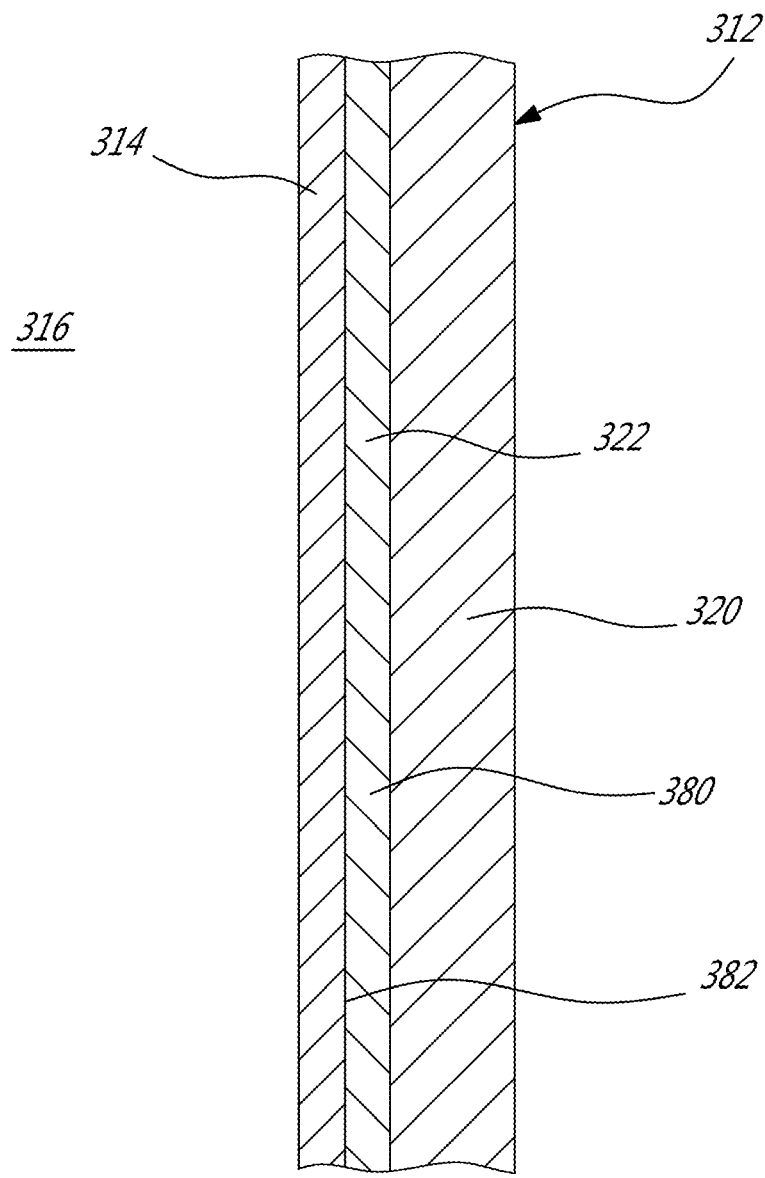

BATHTUB HAVING AT LEAST ONE WINDOW AND METHOD OF MAKING A WINDOW IN A BATHTUB

FIELD

The improvements generally relate to a bathtub and more specifically to a bathtub having a lighting system for lighting an interior of the bathtub.

BACKGROUND

A bathtub generally has a wall defining a cavity for receiving water therein. Different types of wall exist. In some types, the wall has a translucent inner layer which is apparent to the user and which faces water inside the cavity. However, the wall is subjected to different norms and mechanical resistance is an important factor to consider. Accordingly, depending on the type of wall, the translucent inner layer is either reinforced by an opaque external reinforcement layer (e.g., fiberglass) or simply too thick to provide any useful level of translucence.

Although existing bathtub are satisfactory to a certain degree, there remains room for improvement, especially in providing bathtub with a wall across which the cavity can be satisfactorily lit while still providing sufficient mechanical resistance.

SUMMARY

In accordance with one aspect, there is provided a bathtub comprising a wall having a translucent inner layer defining a cavity for receiving water; and at least one translucent outer reinforcement member secured to a portion of the translucent inner layer, and forming at least one window with the corresponding portion of the translucent inner layer, a corresponding light source facing the translucent outer reinforcement member for lighting through the window, into the cavity, the wall further having an outer reinforcement layer covering the translucent inner layer around the at least one window.

In accordance with another aspect, there is provided a method of making a window in a bathtub having a wall with a translucent inner layer defining a cavity for receiving water, the method comprising: securing a translucent outer reinforcement member to a portion of the translucent inner layer, and forming the window with the portion of the translucent inner layer; applying an outer reinforcement layer over the translucent inner layer and around the at least one window; and mounting a light source with respect to the translucent outer reinforcement member, for emitting light through the window and into the cavity.

In accordance with another aspect, there is provided a bathtub comprising a wall having a structural layer of translucent material defining a cavity for receiving water, at least one window including an aperture recessed from an outer face of the structural layer towards the cavity, a translucent reinforcement member moulded within the aperture, and a light source facing the translucent reinforcement member for lighting through the window, into the cavity.

In accordance with another aspect, there is provided a method of making a window in a bathtub having a structural layer of translucent material defining a cavity for receiving water, the method comprising: recessing an aperture from an outer face of the structural layer towards the cavity; and moulding a translucent reinforcement member within the aperture.

In accordance with another aspect, there is described a bathtub comprising a wall having a translucent inner layer defining a cavity for receiving water; an intermediate lightable layer applied on the translucent inner layer, and an outer reinforcement layer secured to the intermediate lightable layer, the intermediate lightable layer facing the translucent inner layer for lighting the cavity therethrough. In some embodiments, the intermediate lightable layer can be provided in the form of a lightable paint sprayed onto the translucent inner layer before application of the outer reinforcement layer thereon.

Many further features and combinations thereof concerning the present improvements will appear to those skilled in the art following a reading of the instant disclosure.

DESCRIPTION OF THE FIGURES

In the figures,

FIG. 1 is an oblique view of an example of a bathtub with windows, in accordance with an embodiment;

FIG. 7 is an image showing two examples of light sources, provided in the form of arrays of light-emitting diodes;

FIG. 8 is a sectional view of an example of a bathtub wall having a structural layer of translucent material with a window molded therein, in accordance with another embodiment;

FIG. 9 is a sectional view of another example of a bathtub wall having a structural layer of translucent material with a window molded therein, in accordance with another embodiment; and FIG. 10 is a sectional view of another example of a bathtub wall including an intermediate lightable layer, in accordance with another embodiment.

DETAILED DESCRIPTION

Figure 2A:
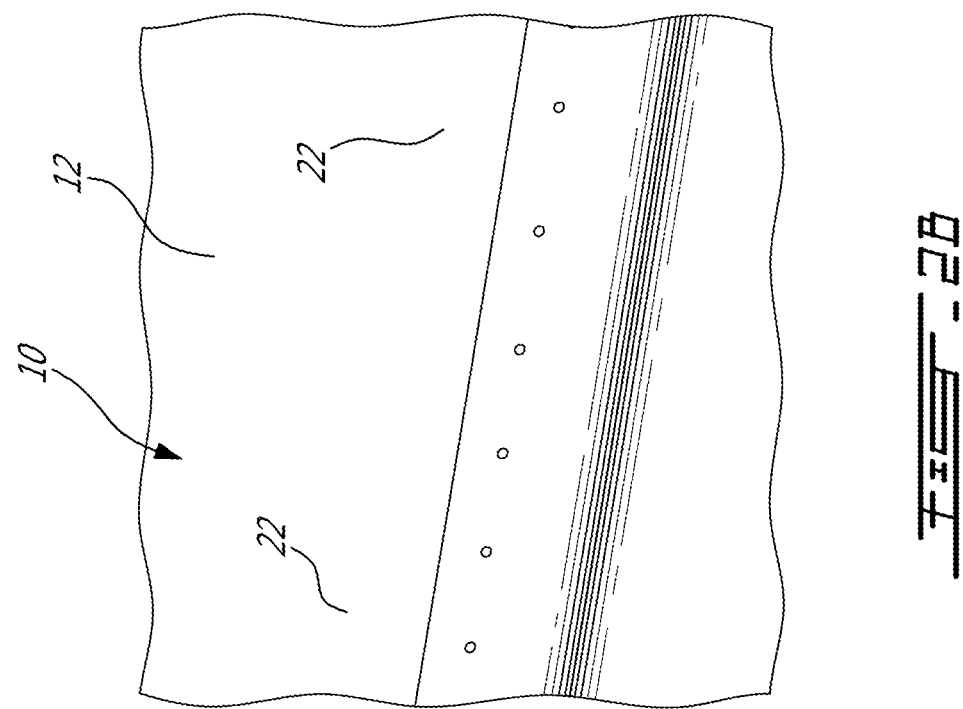
FIG. 2A is an image showing a cavity of the bathtub of FIG. 1, showing some windows when lit.

FIG. 1 shows an example of a bathtub 10 adapted to provide luminotherapeutic and/or chromatherapeutic treatments. As depicted, the bathtub 10 has a wall 12 with a translucent inner layer 14 defining a cavity 16 for receiving water 18, and an outer reinforcement layer 20 covering the translucent inner layer 14.

In this example, the translucent inner layer 14 includes acrylic whereas the outer reinforcement layer 20 includes fiberglass, a type of fiber-reinforced plastic where the reinforcement fiber is specifically glass fiber and where the plastic can be a thermoset polymer such as epoxy, polyester resin, and/or vinylester and/or a thermoplastic. However, in other examples, the outer reinforcement layer can include acrylonitrile butadiene styrene (ABS) plastic or any other suitable reinforcement layer.

In this example, the bathtub 10 is provided with three windows 22 on each of the lateral sides 24a and 24b of the bathtub 10. However, it will be understood that any suitable number of windows can be provided to either one or both of the lateral sides 24a and 24b of the bathtub 10 in alternate embodiments.

One or more light sources 26 face corresponding ones of the windows 22 for lighting the cavity 16 through corresponding ones of the windows 22. As shown, the light sources 26 can be powered by a power supply 28 via wires 30.

FIG. 2A shows an image of the bathtub 10 when some of the windows 22 are lit to provide clean-cut illuminated windows 22 in the wall 12. Such windows 22 can be advantageously used in luminotherapeutic and/or chromatherapeutic treatments where a bather can see its environment lit at different intensities and/or in different colors.

Figure 2B:
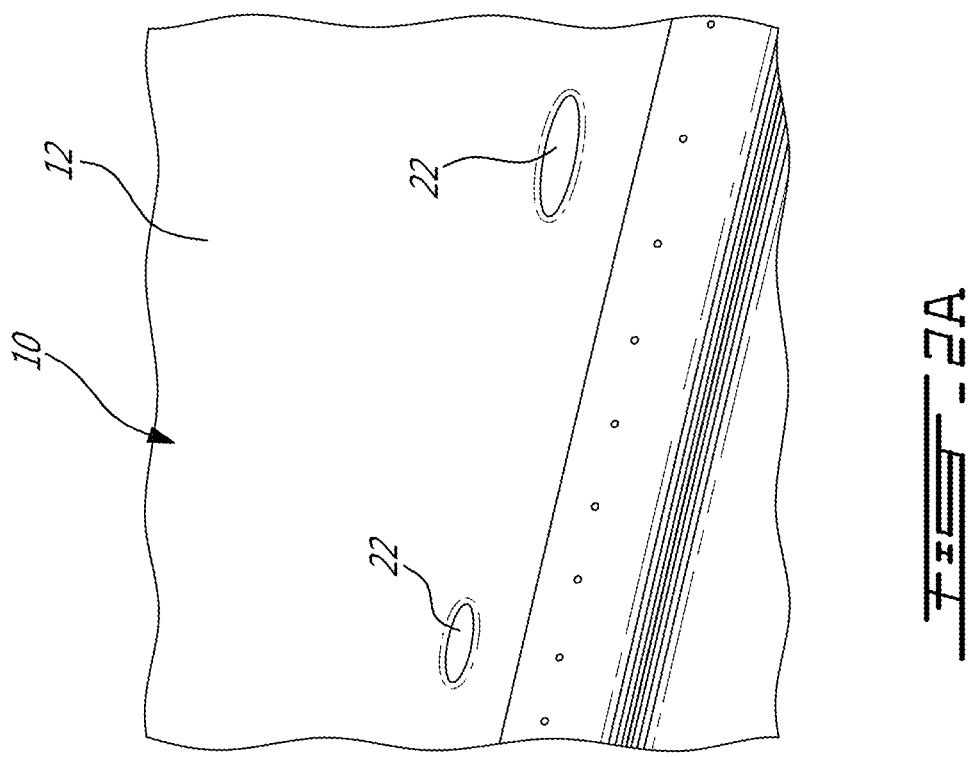
FIG. 2B is an image showing a cavity of the bathtub of FIG. 1, showing some windows when not lit.

In contrast, FIG. 2B shows an image of the bathtub 10 where the windows 22 are not lit. In this latter case, the windows 22 in the wall 12 are imperceptible to the human eye at a given distance. Such windows 22 have been found aesthetically pleasing to the eye as well as easy to clean, which is of importance for bathtubs used in hospitals or any other medical infrastructure.

Figure 3:
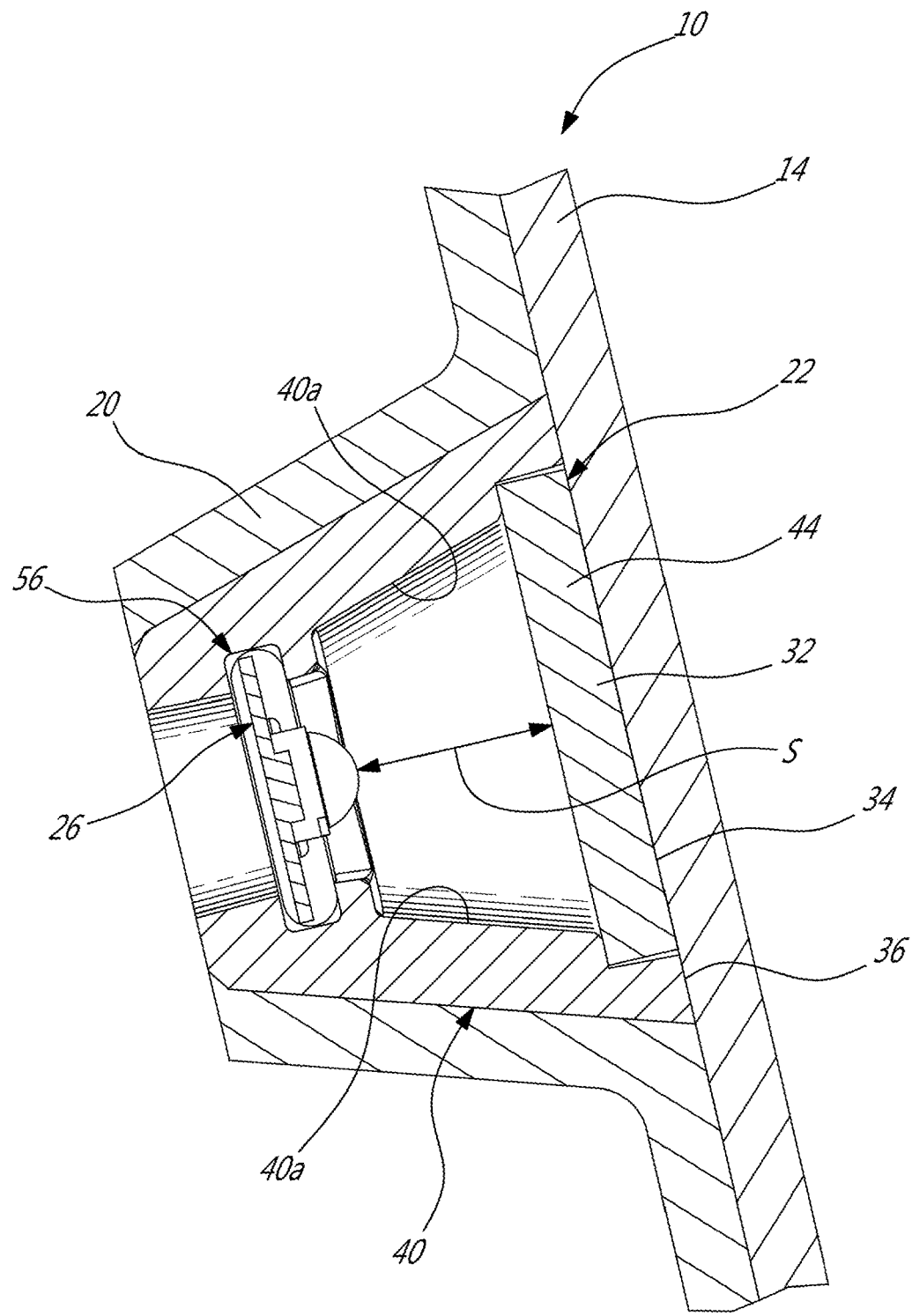
FIG. 3 is a sectional view of one of the windows of FIG. 1, taken along lines 3-3 of FIG. 1, in accordance with an embodiment.

FIG. 3 shows a sectional view of one of the windows 22 of the bathtub 10 of FIG. 1, as taken along line 3-3 of FIG. 1. As depicted, the bathtub 10 has a translucent outer reinforcement member 32 secured to a portion 34 of the translucent inner layer 14. As a result, the translucent outer reinforcement member 32 forms the window 22 with the portion 34 of the translucent inner layer 14.

In this specific embodiment, the translucent outer reinforcement member 32 is adhered to the portion 34 of the translucent inner layer 14 via a translucent adhesive 36. However, the translucent adhesive 36 is optional. For instance, in some other embodiments, the translucent outer reinforcement member 32 is moulded directly onto the portion 34 of the translucent inner layer 14, in which case the translucent outer reinforcement member 32 is secured to the portion 34 via a chemical bond.

As illustrated, the outer reinforcement layer 20 covers the translucent inner layer 14 around the window 22. In other words, the outer reinforcement layer 20 covers the translucent inner layer 14 everywhere but over the window 22. Such construction can allow the wall 12 to exhibit a satisfactory mechanical resistance while allowing the cavity 16 to be lit through the windows 22.

Figure 4:
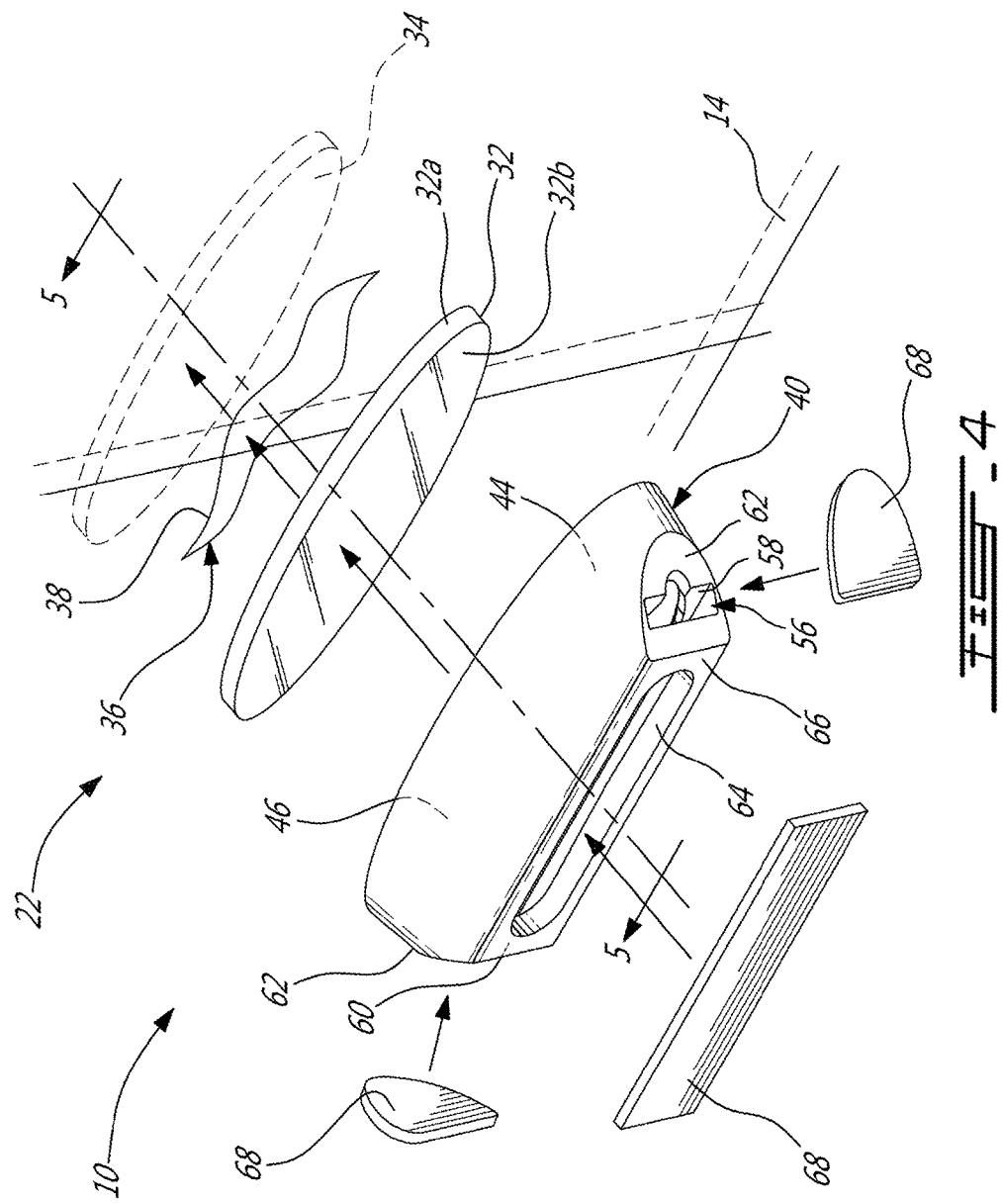
FIG. 4 is an exploded view of the window of FIG. 3, prior to application of the outer reinforcement layer.

Reference is now made to FIG. 4, which shows an exploded view of the window 22 of FIG. 3, shown prior to application of the outer reinforcement layer 20. In this example, the translucent adhesive 36 is provided in the form of a bead 38 which is applied either on an inner face 32a of the translucent outer reinforcement member 32 or on the portion 34 of the translucent inner layer 14.

As the inner face 32a of the translucent outer reinforcement member 32 is pressed against the portion 34 of the translucent inner layer 14, the bead 38 of the translucent adhesive 36 can evenly distribute itself between the translucent outer reinforcement member 32 and the portion 34 of the translucent inner layer 14 in a manner avoiding formation of bubbles. Avoiding such bubbles can be a key in providing window that is aesthetically pleasing to the eye, especially when the window is not lit.

The translucent outer reinforcement member 32 can include polycarbonate, acrylic, poly(methyl methacrylate) (PMMA), styrene-butadiene copolymer (SBC) or any other suitable translucent reinforcement materials. In this embodiment, the translucent outer reinforcement member 32 is a slab polycarbonate shaped in a desired form. The translucent outer reinforcement member 32 can have a thickness ranging between 50 to 250 thousandths of an inch. In this example, however, the translucent outer reinforcement member 32 has a thickness of 125 thousandths of an inch. The shape of the translucent outer reinforcement member 32 generally follows the shape of the translucent inner layer 14. For instance, if the shape of the translucent outer reinforcement member 32 is flat, it should be positioned on a flat portion of the translucent inner layer 14 of the bathtub 10, to avoid aesthetic defects to be visible from inside the bathtub 10.

Figure 5:
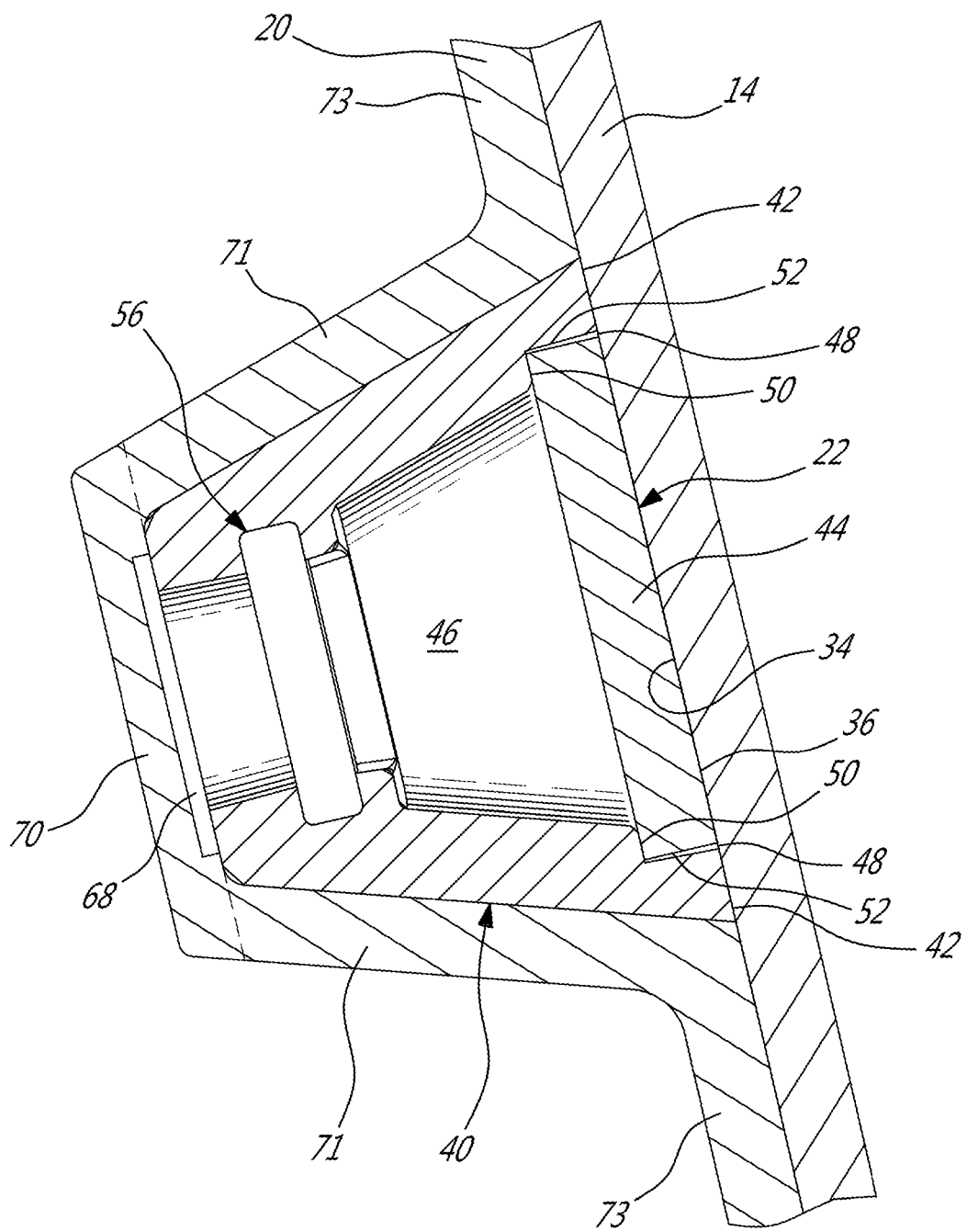
FIG. 5 is a sectional view of the window of FIG. 4, taken along line 5-5 of FIG. 4, after application of the outer reinforcement layer.

In this specific example, the window 22 is provided with a housing 40. As best seen in FIG. 5, the housing 40 has a base 42 in which is defined a first opening 44 which leads to a chamber 46 for housing the corresponding light source (not shown in FIG. 5). As can be seen, in this embodiment, the base 42 is planar. However, the base 42 can be shaped differently in other embodiments.

In this embodiment, a periphery 48 of the first opening 44 defines a seat 50 for snugly receiving the translucent outer reinforcement member 32. In other words, the translucent outer reinforcement member 32 can be press-fitted into the seat 50 of the housing 40.

A seal 52 can be provided in the seat 50 so that the translucent outer reinforcement member 32 be sealingly received in the seat 50. The seal 52 can be provided in the form of an O-ring, a bead of adhesive or any other suitable alternative. The seal 52 can help prevent the plastic such as the resin from accessing the chamber 46 of the housing 40 during application of the outer reinforcement layer 20.

As illustrated, the housing 40 is further configured to maintain the corresponding light source spaced from the translucent outer reinforcement member 32 by a spacing distance. The spacing distance between the corresponding light source and the window 22 can help providing a diffuse lighting inside the cavity of the bathtub. For that purpose, in this embodiment, the housing 40 has a light source guide 56 extending parallel to the translucent outer reinforcement member 32 and spaced from it.

Referring back to FIG. 4, the light source guide 56 extends between a second opening 58 of the housing 40 and a third opening 60 of the housing 40, which are both defined in a corresponding planar surface 62. Each one of the openings 58 and 60 can allow a light source to be slid inside the chamber 46 of the housing 40 along the light source guide 56.

The housing 40 can also have a fourth opening 64, parallel to the first opening 44, defined in a corresponding planar surface 66, opening the chamber 46 of the housing 40 to the air for allowing heat generated by the corresponding light source to be dissipated, for instance.

In this example, a sealing cover 68 is applied on the planar surfaces 62 and 66 to seal the second, third and fourth openings 58, 60 and 64. In this example, the sealing cover 68 can be provided in the form of a tape. As can be understood, the sealing cover 68 can help prevent the plastic such as the resin from accessing the chamber 46 of the housing 40 during application of the outer reinforcement layer 20.

As shown in FIG. 5, the outer reinforcement layer 20 is applied on the translucent inner layer 14, onto the housing 40 and consequently, around the translucent outer reinforcement member 32.

It can be understood that in this embodiment, the outer reinforcement layer 20 completely covers the housing 40 and further maintains the housing 40, and the corresponding translucent outer reinforcement member 32 firmly pressed against the portion 34 to the translucent inner layer 14. However, in some other embodiments, the outer reinforcement layer 20 is applied on the translucent inner layer 14 and around the window 22, such that the outer reinforcement layer 20 surrounds the window 20 but does not cover the housing 40. For instance, in these embodiments, portions 70 and 71 of the outer reinforcement layer 20 are omitted, leaving only portions 73 of the outer reinforcement layer 20 around the window 22.

After application of the outer reinforcement layer 20, the second, third and fourth openings 58, 60 and 64 of the housing 40 are closed, and the chamber 46 of the housing 40 is inaccessible. Accordingly, appropriate portions of the outer reinforcement layer 20 that cover the sealing cover 68 are removed to provide access to the second, third and fourth openings 58, 60 and 64 of the housing 40. For instance, portion 70 of the outer reinforcement layer 20 is to be removed to provide access of the fourth opening 64. The removal of such portions of the outer reinforcement layer 20 can be made by buffing or grinding given portions of the outer reinforcement layer 20 for a given period of time.

Figure 6:
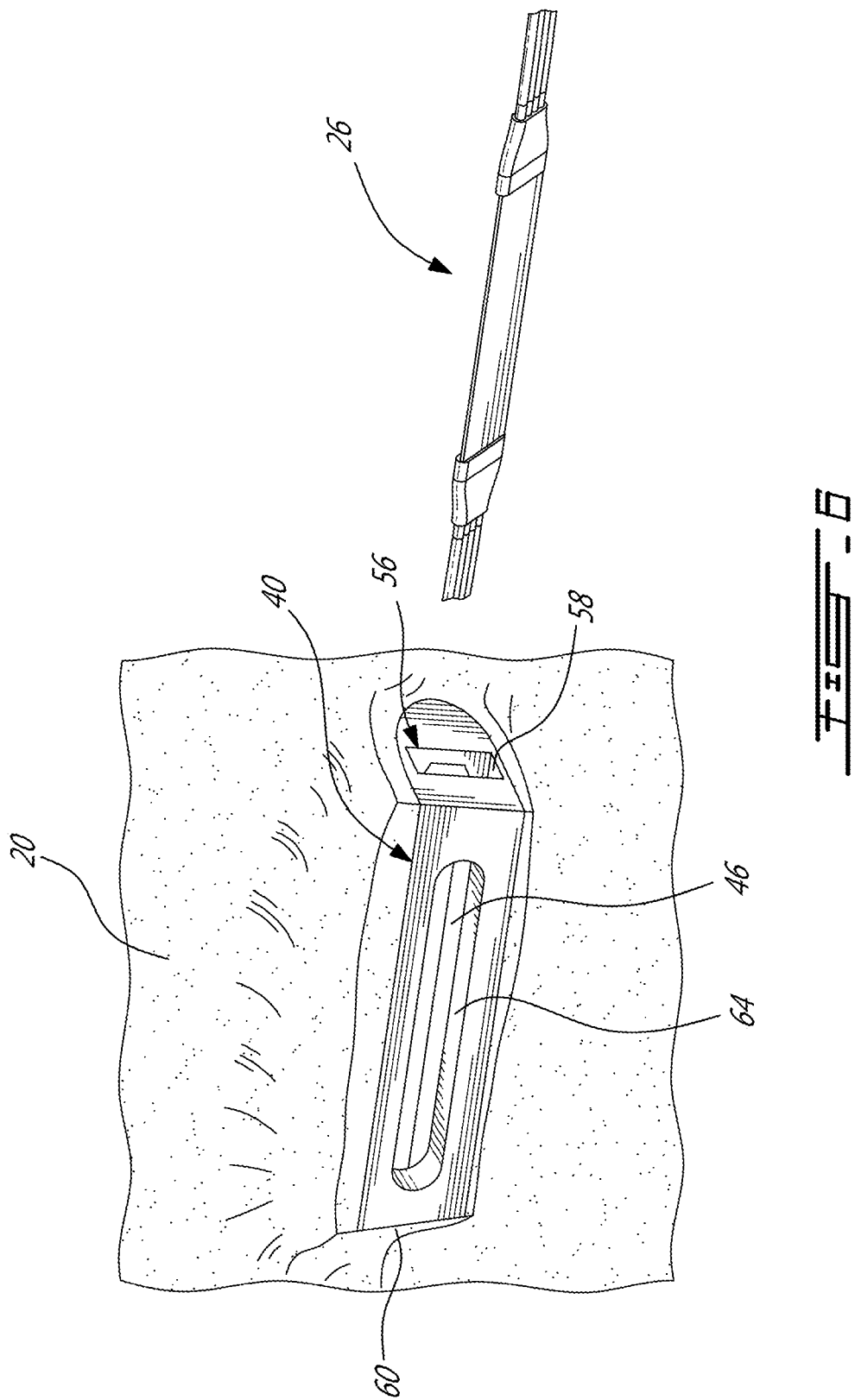
FIG. 6 is an image showing an oblique view of the window of FIG. 3.

FIG. 6 shows an image of the housing 40 with its second, third and fourth openings 58, 60 and 64 rendered accessible by removal of appropriate portions of the outer reinforcement layer 20. Accordingly, the corresponding light source 26 can be slid in the chamber 46 of the housing 40 via either one of the second opening 58 or the third opening 60, resulting in the window 22 shown in FIG. 3. In this case, the light source 26 is slidably received in the housing 40. The light source 26 need not be slid into the housing 40. For instance, in alternate embodiments, the light source 26 is inserted into the housing 40 via the first opening 44 of the housing 40 prior to providing the translucent outer reinforcement member 20 into the seat 50 of the housing 40.

As best seen in FIG. 3, the housing 40 is configured to maintain the corresponding light source 26 spaced from the translucent outer reinforcement member 32 by a spacing distance S, which can help in providing a diffuse lighting inside the cavity of the bathtub. In this embodiment, a spacing distance S of 0.5 inch has been found satisfactory.

As can be seen in this example, the housing 40 has an internal surface 40a inverse tapering from the corresponding light source 26 to the first opening 44. This inverse tapering shape can help in guiding the light emitted from the corresponding light source 26 towards the translucent outer reinforcement member 32. In some embodiments, the internal surface 40a is reflective so as to further guide the light emitted from the corresponding light source 26 towards the translucent outer reinforcement member 32. The internal surface 40a can be made reflective by coloring it in white, in pale grey, in pale beige, the latter of which has been found to provide an aesthetically pleasing appearance when the window 22 is lit. In the alternative, the internal surface 40a can be polished or provided with a metallic finish. Such a metallic finish can be provided by applying a metallic paint inside the housing 40 and/or providing metallic walls therein.

FIG. 7 shows examples of two light sources 26a and 26b that can be slid into the light source guide 56 of the housing 40 during installation. As depicted, the two light sources 26a and 26b are provided in the form of a respective one of first and second arrays of light-emitting diodes (LEDs) 74a and 74b. The first and second arrays of LEDs 74a and 74b differ in their linear densities of LEDs. The first array of LEDs 74a has a first linear density of LEDs which is greater than a second linear density of LEDs of the second array of LEDs 74b. More specifically, the first linear density of LEDs can be two LEDs per inch whereas the second linear density of LEDs can be one LED per inch. In other words, a spacing distance d1 between two LEDs of the first array of LEDs 74a is smaller than a spacing distance d2 between two LEDs of the first array of LEDs 74b. For instance, d1 can be 0.5 inch whereas d2 can be 1 inch. Other linear densities of LEDs can also be used. Although the light sources are shown as being arrays of N LEDs, where N is the total number of LEDs of the array, it is contemplated that the light sources can include a matrix of N×M LEDs, where N×M is the total number of LEDs of the matrix.

FIG. 8 is a sectional view of an example of a bathtub wall 112 defining a cavity 116 for receiving water. As depicted, the wall 112 has a structural layer 114 of translucent material such as acrylic. In this embodiment, the structural layer 114 is said to be structural because the layer 114 is thick enough to provide structure but too thick to provide any useful level of translucence. In this example, the structural layer 114 has one window 122 including an aperture 111 recessed from an outer face 114b of the structural layer 114 towards the cavity 116, leaving an inner translucent member 113. A translucent reinforcement member 132 is moulded within the aperture 111 to form the window 122. As shown in this embodiment, a light source 126 faces the translucent reinforcement member 132 for lighting through the window 122 and into the cavity 116.

FIG. 9 is a sectional view of another example of a bathtub wall 212. In contrast with the bathtub wall 112 described with reference to FIG. 10, the aperture 211 extends through the structural layer 214 of the translucent material of the bathtub wall 212, such that the inner translucent member 113 is omitted. Similarly, a translucent reinforcement member 232 is moulded within the aperture 211 to form the window 222. As depicted, a light source 226 faces the translucent reinforcement member 232 for lighting through the window 222.

FIG. 10 is a sectional view of another example of a bathtub wall 312. In this specific embodiment, the bathtub wall 312 has a translucent inner layer 314 defining a cavity 316 for receiving water. The bathtub wall 312 has an intermediate lightable layer 380 applied on the translucent inner layer 314, and an outer reinforcement layer 320 secured to the intermediate lightable layer 380. As shown, the intermediate lightable layer 380 faces the translucent inner layer 314 for lighting the cavity 316 therethrough. In such an example, a resulting window 322 extends over a significant portion of the bathtub wall 312. In some embodiments, the window 322 extends over the whole bathtub. In some embodiments, the intermediate lightable layer 380 can be provided in the form of a lightable paint 382 sprayed onto the translucent inner layer 314 before application of the outer reinforcement layer 320 thereon.

As can be understood, the examples described above and illustrated are intended to be exemplary only. For instance, the housing can be omitted in certain embodiments. In these embodiments, the outer reinforcement layer is applied simply around the translucent outer reinforcement member in a manner that the outer reinforcement layer maintains the translucent outer reinforcement member into position. Although the portion of the translucent inner layer is shown to be relatively small compared to the size of the bathtub in the illustrated embodiment, it is intended that the portion of the translucent inner layer, which is part of the window, can be considerably larger than what is shown in the illustrated embodiment. The materials of the translucent outer reinforcement member and of the outer reinforcement layer can vary from an embodiment to another. For instance, in the illustrated embodiment, the translucent outer reinforcement member includes polycarbonate whereas the outer reinforcement layer includes fiber glass. However, in another embodiment, the translucent outer reinforcement member includes PMMA whereas the outer reinforcement layer includes ABS plastic. The scope is indicated by the appended claims.

What is claimed is:

1. A bathtub comprising a wall having a translucent inner layer defining a cavity for receiving water; and at least one translucent outer reinforcement member secured to a portion of the translucent inner layer, and forming at least one window with the corresponding portion of the translucent inner layer, a corresponding light source facing the translucent outer reinforcement member for lighting through the window, into the cavity, the wall further having an outer reinforcement layer covering the translucent inner layer around the at least one window.

2. The bathtub of claim 1 wherein the at least one translucent outer reinforcement member is adhered to the portion of the translucent inner layer via a translucent adhesive.

3. The bathtub of claim 1 wherein the at least one window further comprises a housing positioned against the corresponding translucent outer reinforcement member, the housing having a base in which is defined a first opening leading to a chamber for housing the corresponding light source.

4. The bathtub of claim 3 wherein the housing is at least partially covered by the outer reinforcement layer.

5. The bathtub of claim 3 wherein a periphery of the first opening defines a seat for snugly receiving the translucent outer reinforcement member.

6. The bathtub of claim 5 wherein the translucent outer reinforcement member is sealingly received in the seat via a seal.

7. The bathtub of claim 3 wherein the housing is configured to maintain the corresponding light source spaced from the translucent outer reinforcement member.

8. The bathtub of claim 7 wherein the housing has a light source guide extending between a second opening of the housing and a third opening of the housing, parallel to the corresponding translucent outer reinforcement member and spaced therefrom, for slidably receiving the corresponding light source.

9. The bathtub of claim 8 wherein the corresponding light source has an array of light-emitting diodes.

10. The bathtub of claim 3 wherein the housing has an internal surface inverse tapering from the corresponding light source to the first opening.

11. The bathtub of claim 10 wherein the internal surface of the housing is reflective.

12. The bathtub of claim 1 wherein the translucent outer reinforcement member includes polycarbonate.

13. The bathtub of claim 1 wherein the translucent inner layer includes acrylic.

14. The bathtub of claim 1 wherein the outer reinforcement member includes fiberglass.

15. A method of making a window in a bathtub having a wall with a translucent inner layer defining a cavity for receiving water, the method comprising:
  securing a translucent outer reinforcement member to a portion of the translucent inner layer, and forming the window with the portion of the translucent inner layer;
  applying an outer reinforcement layer over the translucent inner layer and around the at least one window; and
  mounting a light source with respect to the translucent outer reinforcement member, for emitting light through the window and into the cavity.

16. The method of claim 15 wherein said securing the translucent outer reinforcement member comprises adhering the translucent outer reinforcement member to the portion of the translucent inner layer via a translucent adhesive.

17. A bathtub comprising a wall having a structural layer of translucent material defining a cavity for receiving water, at least one window including an aperture recessed from an outer face of the structural layer towards the cavity, a translucent reinforcement member moulded within the aperture, and a light source facing the translucent reinforcement member for lighting through the window, into the cavity.

18. The bathtub of claim 17 wherein the aperture recesses through the structural layer.

* * * * *